United States Patent

Ryba et al.

Patent Number: 4,992,583
Date of Patent: Feb. 12, 1991

[54] PROCESS FOR SYNTHESIZING N-CHLOROTHIO-SULFONAMIDES

[75] Inventors: Steven M. Ryba, Norton; Timothy A. Sabo, Southington, both of Ohio

[73] Assignee: The Goodyear Tire & Rubber Company, Akron, Ohio

[21] Appl. No.: 294,033

[22] Filed: Jan. 6, 1989

[51] Int. Cl.$^5$ ............................................. C07C 381/00
[52] U.S. Cl. .................................. 562/821; 562/822; 564/91
[58] Field of Search ................... 562/821, 822; 564/91

[56] References Cited

U.S. PATENT DOCUMENTS 3,360,542 12/1967 Kühle et al. ............................ 560/18
3,915,907 10/1975 Hopper ..................................... 564/91

Primary Examiner—Paul J. Killos
Attorney, Agent, or Firm—Bruce J. Hendricks

[57] ABSTRACT

The present invention relates to a process for synthesizing N-chlorothio-sulfonamides of the formula:

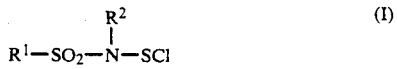

comprising reacting a N,N'-dithiobis(sulfonamide) of the formula:

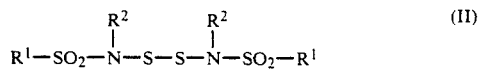

with chlorine gas or sulfuryl chloride in the presence of a liquid solvent comprising a N-chlorothio-sulfonamide of formula I, wherein $R^1$ and $R^2$ are independently selected from the group consisting of alkyl radicals having from about 1 to about 20 carbon atoms, aralkyl radicals having 7 to 20 carbon atoms, cycloalkyl radicals having from about 5 to about 20 carbon atoms, phenyl radicals, alkaryl radicals having from about 7 to 20 carbon atoms, and haloaryl radicals having about 6 to about 10 carbon atoms and where $R^1$ is also selected from radicals having the formula:

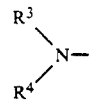

wherein $R^3$ and $R^4$ are individually selected from said alkyl, aralkyl, cycloalkyl, phenyl, alkaryl and haloaryl radicals and wherein $R^3$ and $R^4$ can be joined together to represent radicals selected from $-(CH_2)_n-$, where n is an integer of 4 to 7 and $-(CH_2)_2O-(CH_2)_2-$.

15 Claims, No Drawings

PROCESS FOR SYNTHESIZING N-CHLOROTHIO-SULFONAMIDES

FIELD OF THE INVENTION

The present invention relates to a process for the synthesis of N-chlorothio-sulfonamides from a N,N'-dithiobis(sulfonamide) wherein the solvent for the synthesis is the desired end product, N-chlorothio-sulfonamide.

BACKGROUND OF THE INVENTION

U.S. Pat. No. 3,915,907, discloses that N-chlorothio-sulfonamides are particularly useful as a rubber additive. Since the issuance of U.S. Pat. No. 3,915,907, the demand for N-chlorothio-sulfonamides has been increasing and extensive research has been conducted to find an economical method of producing N-chlorothiosulfonamides.

West German Patent 1,101,407 discloses a method for the preparation of N-chlorothio-sulfonamides from N,N'-dithiobis(sulfonamides). The method of West German Patent No. 1,101,407 involves reacting the N,N'-dithiobis(sulfonamide) with chlorine in the presence of an organic inert solvent such as carbon tetrachloride or chloroform. Unfortunately, the prior art method suffers from many disadvantages.

One of the disadvantages is the solvent stripping operations are slow and involve up to 6 hours total batch time. To prevent the thermal degradation of the end product, low temperatures are required for stripping. The slow procedure contributes to the expense of the process. Another major disadvantage is the suspected carcinogenic nature of many chlorinated organic solvents.

In view of the ever increasing demand for chlorothio-sulfonamides and the dangers in preparing these compounds, there is a need for a safer and more efficient method for the preparation of these compounds.

SUMMARY OF THE INVENTION

There is disclosed a process for synthesizing N-chlorothio-sulfonamides of the formula:

comprising reacting a N,N'-dithiobis(sulfonamide) of the formula:

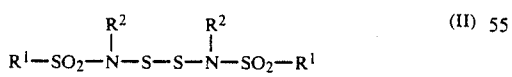

with chlorine gas or sulfuryl chloride in the presence of a liquid solvent comprising a N-chlorothiosulfonamide of formula I, wherein $R^1$ and $R^2$ are independently alkyl radicals having from about 1 to about 20 carbon atoms, aralkyl radicals having 7 to 20 carbon atoms, cycloalkyl radicals having from about 5 to 20 carbon atoms, phenyl radicals, and alkaryl radicals having from about 7 to 20 carbon atoms, and haloaryl radicals having about 6 to about 10 carbon atoms and where $R^1$ is also selected from radicals having the formula:

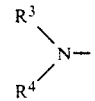

wherein $R^3$ and $R^4$ are individually selected from said alkyl, aralkyl, cycloalkyl, phenyl, alkaryl and haloaryl radicals and wherein $R^3$ and $R^4$ can be joined together to represent radicals selected from $-(CH_2)_n-$ where n is an integer of 4 to 7 and $-(CH_2)_2O-(CH_2)_2-$.

DETAILED DESCRIPTION OF THE INVENTION

The present invention relates to a new and improved process for synthesizing a N-chlorothio-sulfonamide of the above formula I. Preferably, $R^1$ and $R^2$ are selected from alkyl radicals having 1 to 6 carbon atoms, phenyl radicals, monoalkyl substituted phenyl radicals having 7 to 10 carbon atoms and dialkyl substituted phenyl radicals having from 8 to 11 carbon atoms where such alkyl substituent or substituents are radicals selected from the group consisting of methyl, ethyl, and all isomeric forms of propyl and butyl radicals, and from the p-chlorophenyl radical. Representative of radicals suitable for $R^1$ are radicals selected from methyl, tert butyl, cyclohexyl, 2-eicosyl, benzyl, 2(p-n-undecylphenyl)-2-propyl, phenyl, 1-naphthyl, p-tolyl, 3-ethyl-4-(n-dodecyl) phenyl, p-chlorophenyl and 3-chloro-4-(n-butyl)-phenyl radicals.

Representative of radicals suitable for $R^2$ are methyl, tert butyl, 1-eicosyl, cyclohexyl, benzyl, 1-(p-n-dodecylphenyl)-1-ethyl, phenyl, 1-naphthyl, m-tolyl, 3,4-di(n-heptyl)phenyl, p-bromophenyl and 3-chloro-4-(n-butyl) phenyl radicals.

Representative examples of N-chlorothio-sulfonamides which can be produced according to the present invention are N-chlorothio-N-methyl-methanesulfonamide, N-chlorothio-N-methyl-benzenesulfonamide, N-chlorothio-N-methyl-p-toluenesulfonamide, N-chlorothio-N-ethyl-p-toluenesulfonamide, N-chlorothio-N-methyl-ethanesulfonamide, N-chlorothio-N-phenyl-p-toluenesulfonamide, N-chlorothio-N-(2-propyl)-methanesulfonamide, N-chlorothio-N-(1-propyl)-p-chlorobenzenesulfonamide, N-chlorothio-N-phenyl-methanesulfonamide, N-chlorothio-N,N',N'-trimethylsulfamide, N-chlorothio-N-methyl-N',N'-(pentamethylene)sulfamide, N-chlorothio-N-methyl-N',N'-diethylsulfamide and N-chlorothio-N-phenyl-benzenesulfonamide.

The N-chlorothio-sulfonamides are derived from a N,N'-dithiobis(sulfonamide) compound of the formula:

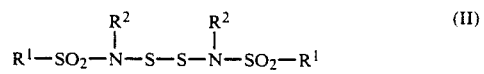

wherein $R^1$ and $R^2$ are as described above. The N,N'-dithiobis(sulfonamide) of formula II may be prepared in accordance with the method disclosed in West German Patent 951,719 which is incorporated by reference in its entirety. The (N,N'-dithiobis(sulfonamide) may also be prepared in accordance with the method taught in U.S. patent application Ser. No. 263,836, filed Oct. 26, 1988, which is incorporated by reference in its entirety. U.S. patent application Ser. No. 263,836 discloses a method wherein a sulfonamide is reacted with sulfur monochloride and caustic in a mixed organic-aqueous media. The preparation of the N,N'-dithiobis (sulfonamide) starting material is not a part of the present invention.

The N,N'-dithiobis(sulfonamide) of formula II is reacted with chlorine gas or sulfuryl chloride. For every mole of N,N'-dithiobis(sulfonamide) of formula II, there should be a molar excess of Cl. Therefore, the molar ratio of Cl to the sulfonamide of formula II may range from about at least 1:1 to 4:1. Preferably, the molar ratio Cl to the sulfonamide of formula II ranges from about 1.8:1 to 2.1:1. When the chlorine gas or sulfuryl chloride is added to the reactor, it is preferably done with agitation to the reaction mixture to insure uniform distribution of the reactants.

The N,N'-dithiobis(sulfonamide) of formula II is reacted with chlorine gas or sulfuryl chloride in the presence of a liquid solvent of formula I. The term liquid solvent is intended to mean all N-chlorothio-sulfonamides which are liquid at the reaction temperatures. The amount of liquid solvent initially present may be as little to form a slurry of starting material, however, the slurry should not be so concentrated so that it is too difficult to agitate. On the other hand, the amount of liquid solvent initially present may be in an amount sufficient to dissolve the starting material for reaction with the chlorine gas or sulfuryl chloride. Preferably, the amount of liquid N-chlorothio-sulfonamide that is initially present as a solvent is sufficient to give a 0 to about 50 weight percent slurry of N,N'-dithiobis(sulfonamide). Preferably, the weight percent of the slurry is from about 25 to about 35 percent.

In carrying out the process of the present invention, precaution should be exercised to avoid any water in the reaction vessel. One suitable means of avoiding the entry of water vapor is to use a closed system.

The order of addition of the reagents to the reaction mixture may vary. For example, in one embodiment, all of the N,N'-dithiobis(sulfonamide) may be added to the liquid chlorothio-sulfonamide with the chlorine gas or sulfuryl chloride being added later.

The process of the present invention may be conducted at a variety of reaction temperatures so long as the temperatures are greater than the melting point of the product of formula I so that the solvent remains a liquid. For example, the process may be conducted at a temperature ranging from about 20° C. to about 60° C. Preferably, the reaction temperature will range from about 20° C. to about 40° C. with a range of from 25° C. to about 35° C. being particularly preferred.

As one skilled in the art can appreciate, the present invention may be carried out under a wide range of pressures. Generally speaking, the process of the present invention is carried out at atmospheric pressure.

Upon completion of the reaction, a portion of the product may be removed from the reaction vessel. The remaining product may be used as a solvent for subsequent preparations. As can be appreciated by one skilled in the art having an understanding of the present invention, the lengthy stripping operations of the prior art are eliminated as well as the health concerns when handling potentially carcinogenic solvents.

The present process may be conducted in a batchwise or continuous manner. In either case, one may use a portion of the product for use as a liquid solvent for subsequent preparations.

The reaction vessel should be equipped with a means of agitation, an inlet for the introduction of the reactants and a means of controlling temperature, e.g., cooling and heating means. Preferably, the reactor should be glass-lined or other inert material to minimize corrosion effects of the reactants.

Practice of this invention is further illustrated by reference to the following examples which are intended to be representative rather than restrictive of the scope of the present invention. Properties of the final products, expressed as weight percent were determined by liquid chromatographic analysis.

EXAMPLES 1-11

Preparation of
N-chlorothio-N-methyly-methanesulfonamide

The reaction vessel was a 30 gallon glass-lined reactor equipped with a water jacket, bottom drain, agitator, thermocouple and two charge tanks. To this reactor vessel the following general charging procedure was used. A weighed amount of N-chlorothio-N-methylmethanesulfonamide (CTMBS) was charged to the sealed reactor by using vacuum. The vacuum was broke with dry nitrogen. A weighed amount of N,N'-dimethyl-N,N'-dithiobis benzenesulfonamide (DDBBS) was then charged to the reaction vessel. The mixture was agitated for approximately 10 minutes. The headspace in the reactor was purged with dry nitrogen for 5 minutes. The flow of nitrogen was stopped and the flow of chlorine gas initiated. The chlorine gas was continuously introduced into the reactor for approximately 1 hour until a measured amount had been added. The reactor was maintained at a temperature below 35° C. After the addition of the chlorine gas was complete, the temperature was maintained above 25° C. The reactor was purged with dry nitrogen and a portion of the product removed, weighed and tested by HPLC. The remaining product in the reactor was used as a solvent for the next batch. Table I below lists the amount of CTMBS, chlorine gas and DDBBS that were used in each example, the amount of product CTMBS removed and the purity of the product CTMBS.

TABLE I

| Example | CTMBS Charge (kg.) | DDBBS (kg.) | Cl$_2$ (kg.) | Product CTMBS (kg.) | Purity of Product (%) | Total Batch Time (hrs.) |
|---|---|---|---|---|---|---|
| 1 | 55.51 | 34.25 | 6.50 | 40.55 | 102.3 | 2.0 |
| 2 | 55.71 | 34.25 | 6.50 | 40.55 | 98.4 | 1.75 |
| 3 | 55.91 | 34.25 | 6.50 | 40.55 | 100.7 | 1.50 |
| 4 | 56.10 | 34.25 | 6.50 | 40.55 | 104.2 | 1.75 |
| 5 | 56.30 | 34.25 | 6.50 | 97.05 | 98.5 | 2.00 |
| 6 | 55.51 | 34.25 | 6.30 | 40.55 | 96.9 | 2.00 |
| 7 | 55.51 | 34.25 | 6.30 | 40.55 | 96.5 | 1.75 |
| 8 | 55.51 | 34.25 | 6.30 | 39.37 | 95.8 | 1.50 |
| 9 | 55.51 | 33.86 | 6.30 | 96.85 | 95.0 | 2.00 |
| 10 | 49.21 | 30.31 | 5.28 | 23.43 | 94.5 | 1.50 |
| 11 | 61.37 | 37.80 | 6.50 | 44.29 | 90.3 | 2.00 |
| 12 | 61.37 | 37.80 | 6.50 | 44.29 | 91.9 | 1.50 |

TABLE I -continued

| Example | CTMBS Charge (kg.) | DDBBS (kg.) | Cl₂ (kg.) | Product CTMBS (kg.) | Purity of Product (%) | Total Batch Time (hrs.) |
|---|---|---|---|---|---|---|
| 13 | 61.37 | 37.80 | 6.50 | 44.29 | 94.3 | 1.50 |
| 14 | 61.37 | 37.80 | 6.50 | 44.29 | 93.9 | 2.00 |
| 15 | 61.37 | 27.56 | 4.76 | 43.69 | 97.9 | 2.00 |

As can be appreciated by those skilled in the art having read the above examples, use of the product chlorothio-sulfonamide as the solvent avoids the hazardous use of undesirable organic solvents as well as the long processing times resulting from removal of organic solvents at low temperatures due to the low thermal stability of the product. In addition, a significantly short batch time was involved in the various examples.

While certain representative embodiments and details have been shown for the purpose of illustrating the invention, it will be apparent to those skilled in this art that various changes and modifications may be made therein without departing from the spirit or scope of the invention.

What is claimed is:

1. A process for synthesizing N-chlorothiosulfonamides of the formula:

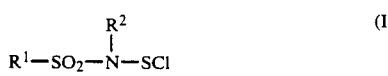

comprising reacting a N,N'-dithiobis(sulfonamide) of the formula:

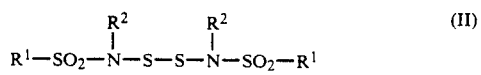

with chlorine gas or sulfuryl chloride in the presence of a liquid solvent consisting of a N-chlorothiosulfonamide of formula I, wherein $R^1$ and $R^2$ are independently selected from the group consisting of alkyl radicals having 1 to 20 carbon atoms, aralkyl radicals having 7 to 20 carbon atoms, cycloalkyl radicals having 5 to 20 carbon atoms, phenyl radicals and alkaryl radicals having 7 to 20 carbon atoms, and haloaryl radicals having about 6 to about 10 carbon atoms and where $R^1$ is also selected from radicals having the formula:

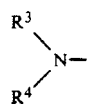

wherein $R^3$ and $R^4$ are individually selected from said alkyl, aralkyl, cycloalkyl, phenyl, alkaryl and haloaryl radicals and wherein $R^3$ and $R^4$ can be joined together to represent radicals selected from $-(CH_2)_n-$, where n is an integer of 4 to 7 and $-(CH_2)_2O-(CH_2)_2-$.

2. The process of claim 1 wherein $R^1$ and $R^2$ are selected from the group consisting of alkyl radicals having 1 to 6 carbon atoms, phenyl radicals, monoalkyl substituted phenyl radicals having 7 to 10 carbon atoms and dialkyl substituted phenyl radicals having from 8 to 11 carbon atoms where such alkyl substituent or substituents are radicals selected from the group consisting of methyl, ethyl, and all isomeric forms of propyl and butyl radicals, and from the p-chlorophenyl radical.

3. The process of claim 2 wherein $R^1$ is selected from the group of radicals consisting of methyl, tert butyl, cyclohexyl, 2-eicosyl, benzyl, 2-(p-n-undecylphenyl)-2-propyl, phenyl, p-chlorophenyl and 3-chloro-4-(n-butyl) phenyl.

4. The process of claim 2 wherein $R^2$ is selected from the group of radicals consisting of methyl, tert butyl, 1-eicosyl, cyclohexyl, benzyl, 1-(p-n-dodecylphenyl)-1-ethyl, phenyl, 1-naphthyl, m-tolyl, 3,4-di-(n-heptyl) phenyl, p-bromophenyl and 3-chloro-4-(n-butyl) phenyl.

5. The process of claim 1 wherein said N-chlorothiosulfonamide is selected from the group consisting of N-chlorothio-N-methyl-methanesulfonamide, N-chlorothio-N-methyl-benzenesulfonamide, N-chlorothio-N-methyl-p-toluenesulfonamide, N-chlorothio-N-ethyl-p-toluenesulfonamide, N-chlorothio-N-methyl-ethanesulfonamide, N-chlorothio-N-phenyl-p-toluenesulfonamide, N-chlorothio-N-(2-propyl)-methanesulfonamide, N-chlorothio-N-(1-propyl)-p-chlorobenzenesulfonamide, N-chlorothio-N-phenyl-methanesulfonamide, N-chlorothio-N,N',N'-trimethylsulfamide, N-chlorothio-N-methyl-N',N'-(pentamethylene)sulfamide, N-chlorothio-N-methyl-N',N'-diethylsulfamide and N-chlorothio-N-phenyl-benzenesulfonamide.

6. The process of claim 5 wherein said N-chlorothiosulfonamide is N-chlorothio-N-methyl-benzenesulfonamide.

7. The process of claim 1 wherein said N,N'-dithiobis(sulfonamide) is N,N'-dimethyl-N,N'-dithiobis(p-toluenesulfonamide).

8. The process of claim 1 wherein said N,N'-dithiobis(sulfonamide) is N,N'-dimethyl-N,N'-dithiobis(benzenesulfonamide).

9. The process of claim 1 wherein chlorine gas is used.

10. The process of claim 1 wherein the amount of liquid N-chlorothio-sulfonamide that is initially present as a solvent is sufficient to give a 0 to about 50 weight percent slurry of N,N'-dithiobis(sulfonamide) of formula II.

11. The process of claim 10 wherein the weight percent ranges from about 25 to about 35 weight percent.

12. The process of claim 1 wherein the reaction is conducted at a temperature above the melting point of the N,N'-dithiobis(sulfonamide) of formula II.

13. The process of claim 1 wherein the reaction is conducted at a temperature ranging from about 20° C. to about 60° C.

14. The process of claim 12 wherein the reaction is conducted at a temperature ranging from about 20° C. to 40° C.

15. The process of claim 1 wherein the reactor is conducted at a temperature ranging from about 25° C. to about 35° C.

* * * * *